(12) United States Patent
McKinney et al.

(10) Patent No.: US 9,409,997 B2
(45) Date of Patent: Aug. 9, 2016

(54) FUNCTIONALIZED GRAPHENE SUBSTRATES

(71) Applicant: NANOTECH BIOMACHINES, INC., Berkeley, CA (US)

(72) Inventors: Jeffrey Alan McKinney, Lafayette, CA (US); William Emerson Martinez, Berkeley, CA (US)

(73) Assignee: Nanotech Biomachines, Inc., Berkeley, CA (US)

( * ) Notice: Subject to any disclaimer, the term of this patent is extended or adjusted under 35 U.S.C. 154(b) by 0 days.

(21) Appl. No.: 14/120,485

(22) Filed: May 23, 2014

(65) Prior Publication Data

US 2015/0004667 A1  Jan. 1, 2015

Related U.S. Application Data

(60) Provisional application No. 61/855,818, filed on May 24, 2013.

(51) Int. Cl.
| | |
|---|---|
| *C07K 17/14* | (2006.01) |
| *C12N 9/96* | (2006.01) |
| *C12N 11/08* | (2006.01) |
| *C12N 11/14* | (2006.01) |
| *C01B 31/04* | (2006.01) |

(52) U.S. Cl.
CPC ............. *C07K 17/14* (2013.01); *C01B 31/0484* (2013.01); *C12N 9/96* (2013.01); *C12N 11/08* (2013.01); *C12N 11/14* (2013.01)

(58) Field of Classification Search
CPC ....................................................... C07K 17/14
See application file for complete search history.

(56) References Cited

FOREIGN PATENT DOCUMENTS

WO  WO 2008/104078 A1  9/2008

OTHER PUBLICATIONS

Pumera, 2011, Graphene in biosensing, Materials Today, 14(7-8): 308-315.*
Kodali et al., 2011, Nonperturbative Chemical Modification of Graphene for Protein Micropatterning, Langmuir, 27(3): 863-865.*
Sardesai et al., 2011, Carbon Nanotube Microwell Array for Sensitive Electrochemiluminescent Detection of Cancer Biomarker Proteins, Anal. Chem., 83: 6698-6703.*

* cited by examiner

*Primary Examiner* — Amber D Steele
(74) *Attorney, Agent, or Firm* — Fenwick & West LLP

(57) ABSTRACT

The present invention is generally directed to functionalized graphene substrates, methods of making such substrates and methods of using such substrates. In one aspect, the present invention provides a graphene substrate. The substrate comprises edge and non-edge regions, and organic or inorganic molecules are bound to the edge regions of the substrate. The organic or inorganic molecules are present on the substrate edges at a population greater than about one molecule per 10,000 nm.

14 Claims, 17 Drawing Sheets

FUNCTIONALIZED GRAPHENE SUBSTRATES

This application claims priority from U.S. Provisional Patent Appl. No. 61/855,818, filed May 24, 2013, entitled, "Functionalized graphene substrates", which is hereby incorporated by reference into this application in its entirety.

FIELD OF THE INVENTION

The present invention is generally directed to functionalized graphene substrates, methods of making such substrates and methods of using such substrates.

BACKGROUND OF THE INVENTION

There have been reports regarding certain chemical properties of graphene. For instance, U.S. Pat. No. 8,388,924, issued Mar. 5, 2013 and entitled "Method for Growth of High Quality Graphene Films", discusses the following: "The present application relates generally to methods for growth of high quality graphene films. In particular, a method is provided for forming a graphene film using a modified chemical vapor deposition process using an oxygen-containing hydrocarbon liquid precursor. Desirably, the graphene films are a single-layer and have a single grain continuity of at least 1 $\mu m^2$." Abstract.

U.S. Pat. No. 8,362,295, issued Jan. 29, 2013 and entitled "Graphene Compositions and Methods for Production Thereof", discusses the following: "Drilling fluids comprising graphenes and nanoplatelet additives and methods for production thereof are disclosed. Graphene includes graphite oxide, graphene oxide, chemically-converted graphene, and functionalized chemically-converted graphene. Derivatized graphenes and methods for production thereof are disclosed. The derivatized graphenes are prepared from a chemically-converted graphene through derivatization with a plurality of functional groups. Derivatization can be accomplished, for example, by reaction of a chemically-converted graphene with a diazonium species. Methods for preparation of graphite oxide are also disclosed." Abstract.

U.S. Pat. No. 8,361,853, issued Jan. 29, 2013 and entitled "Graphene Nanoribbons, Method of Fabrication and Their Use in Electronic Devices", discusses the following: "The present disclosure provides a semiconductor structure including a nanoribbon-containing layer of alternating graphene nanoribbons separated by alternating insulating ribbons. The alternating graphene nanoribbons are parallel to a surface of an underlying substrate and, in some embodiments, might be oriented along crystallographic directions of the substrate. The alternating insulating ribbons may comprise hydrogenated graphene, i.e., graphane, fluorinated graphene, or fluorographene. The semiconductor structure mentioned above can be formed by selectively converting portions of an initial graphene layer into alternating insulating ribbons, while the non-converted portions of the initial graphene form the alternating graphene nanoribbons. Semiconductor devices such as, for example, field effect transistors, can be formed atop the semiconductor structure provided in the present disclosure." Abstract.

U.S. Pat. No. 8,287,699, issued on Oct. 16, 2012 and entitled "Production of Chemically Functionalized Nanographene Materials" discusses the following: "Provided in this invention is a process for producing chemically functionalized nano graphene materials, known as nano graphene platelets (NGPs), graphene nano sheets, or graphene nano ribbons. Subsequently, a polymer can be grafted to a functional group of the resulting functionalized NGPs. In one preferred embodiment, the process comprises (A) dispersing a pristine graphite material and an azide or bi-radical compound in a liquid medium comprising to form a suspension; and (B) subjecting the suspension to direct ultrasonication with to ultrasonic waves of a desired intensity or power level for a length of time sufficient to produce nano graphene platelets and to enable a chemical reaction to occur between the nano graphene platelets and the azide or bi-radical compound to produce the functionalized nano graphene." Abstract.

U.S. Pat. No. 8,221,884, issued Jul. 17, 2012 and entitled "Incorporation of Functionalizing Molecules in Nano-Patterned Epitaxial Graphene Electronics", discusses the following: "In a method of making graphite devices, a thin-film graphitic layer disposed against a preselected face of a substrate is created on the preselected face of the substrate. A preselected pattern is generated on the thin-film graphitic layer. At least one functionalizing molecule is attached to a portion of the graphitic layer. The molecule is capable of interacting with .pi. bands in the graphitic layer." Abstract.

Despite the reports regarding certain chemical properties of graphene, there is still a need in the art for new functionalized graphene substrates, methods of making such substrates and methods of using such substrates.

SUMMARY OF THE INVENTION

In one aspect, the present invention provides a graphene substrate. The substrate comprises edge and non-edge regions, and organic or inorganic molecules are bound to the edge regions of the substrate. The organic or inorganic molecules are present on the substrate at a density greater than about one molecule per 10,000 $nm^2$.

In another aspect, the present invention provides a method of functionalizing a graphene substrate. The method comprises the steps of: a) obtaining a graphene substrate that has edge regions and non-edge regions, wherein the edge regions comprise carboxylic acid moieties, epoxy moieties or hydroxyl moieties; b) reacting the carboxylic acid moieties, epoxy moieties or hydroxyl moieties with a Nu-M, wherein Nu is a nucleophilic moiety and M is an attached organic or inorganic moiety, thereby functionalizing the graphene substrate.

DETAILED DESCRIPTION OF THE INVENTION

Figure 1:
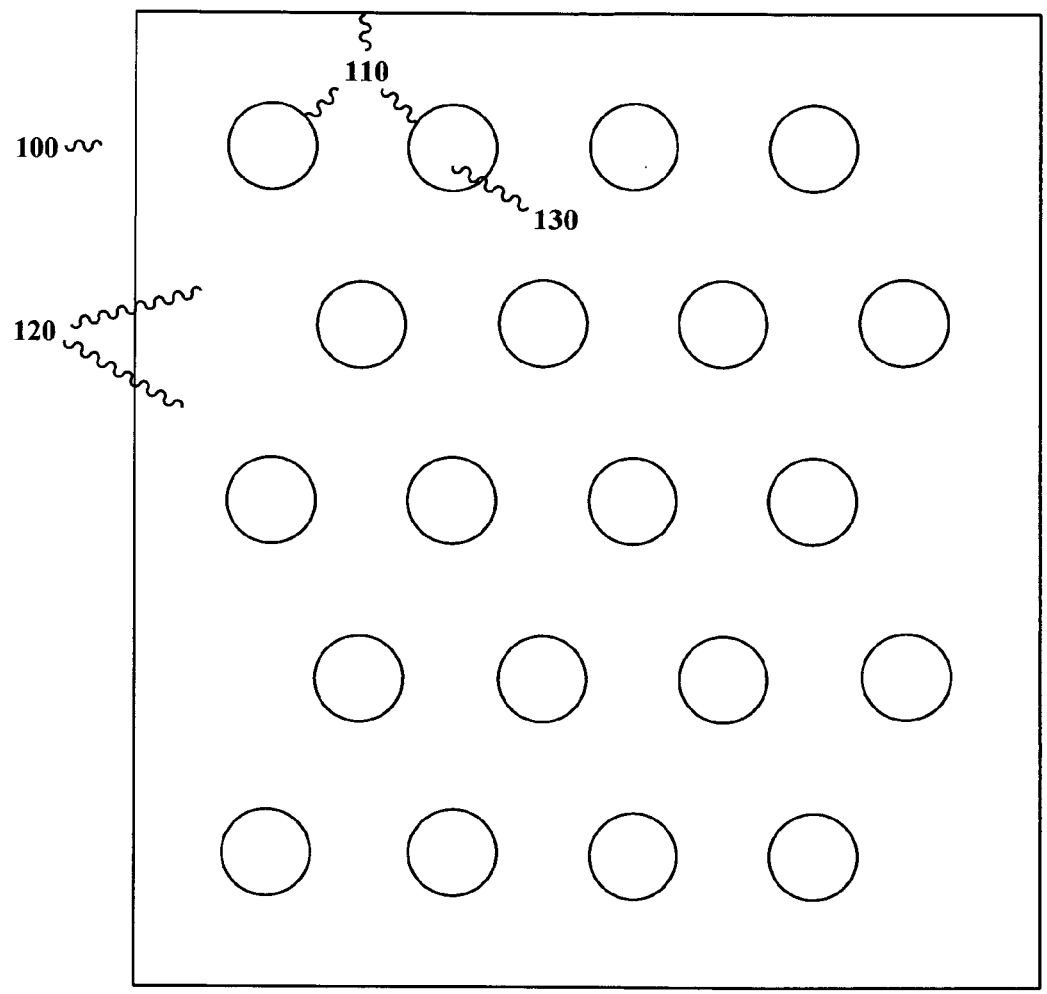
FIG. 1 is an illustration of a graphene substrate (100) having edge (110) and non-edge (120) regions, as well as holes (130) where there is no graphene.

The present invention is generally directed to functionalized graphene substrates, methods of making such substrates and methods of using such substrates.

Definitions

"Amino acid letter code" refers to the one letter code typically used for amino acids: arginine (R); histidine (H); lysine (K); aspartic acid (D); glutamic acid (E); serine (S); threonine (T); asparagine (N); glutamine (Q); cysteine (C); glycine (G); proline (P); alanine (A); valine (V); isoleucine (I); leucine (L); methionine (M); phenylalanine (F); tyrosine (Y); tryptophan (W).

"Antibody" refers to a Y-shaped protein on the surface of B cells that is secreted into the blood or lymph in response to an antigenic stimulus.

"Antibody fragment" refers to part of an antibody comprising an antigen binding domain.

"Aptamer" refers to small, single-stranded nucleic acids that fold into a well-defined three-dimensional structure. They show a high affinity and specificity for their target molecules and inhibit their biological functions. Aptamers are usually discovered/created by selecting them from a large random sequence pool.

"Binding site" refers to a region on a molecule (e.g., protein, DNA, RNA) to which other specific molecules and/or ions form one or more chemical bonds, typically non-covalent bonds.

"Covalently" bound refers to formation of a covalent bond, which involves the sharing of electrons between at least two atoms. The strength of a covalent bond typically ranges from approximately 50 kcal/mol to approximately 100 kcal/mol.

"Edge region" of a graphene substrate refers to a line or border where the graphene substrate ends and either another material or an open space begins. Graphene edge regions typically include oxidized carbon moieties such as carboxylic acids, epoxides and hydroxyl groups.

"Graphene nanomesh" refers to a one atom thick layer of carbon atoms including holes in a repeating structural fashion (e.g., honeycomb structure).

"Graphene nanoribbon" refers to strips of graphene having ultra-thin widths (e.g., <50 nm).

"Graphene substrate" refers to a layer of carbon atoms, typically one, two, three or four atoms thick. There are at least 100 carbon atoms in the substrate. Monolayer graphene refers to a substrate that is one carbon atom thick.

"Hydrogen bond" refers to a noncovalent bond formed by the interaction of a proton on one molecule and an electronegative atom on another. The strength of a hydrogen bond typically ranges from approximately 3 kcal/mol to approximately 10 kcal/mol.

"Inorganic molecule" refers to molecules that do not include carbon atoms.

"Ionically" bound refers to the formation of an ionic bond. The strength of an ionic bond typically ranges from approximately 5 kcal/mol to approximately 10 kcal/mol.

"$K_D$" refers to "dissociation constant", which is a specific type of equilibrium constant that measures the propensity of a larger object to separate (dissociate) reversibly into smaller components, as when a complex falls apart into its component molecules. The dissociation constant is the inverse of the association constant. For a general reaction $$A_xB_y \leftrightharpoons xA + yB$$

in which a complex $A_xB_y$ breaks down into x A subunits and y B subunits, the dissociation constant is defined

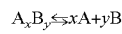

$$K_d = \frac{[A]^x \times [B]^y}{[A_xB_y]}$$

where [A], [B], and [$A_xB_y$] are the concentrations of A, B, and the complex $A_xB_y$, respectively.

"Large molecule therapeutic" refers to an organic molecule of molecular weight greater than 1000 g/mol, where the molecule has been, or is currently, used for a clinical application. Nonlimiting examples of large molecule therapeutic classes include: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; amebicides; aminoglycosides; aminopenicillins; aminosalicylates;

AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinsonism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer; heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracyclic antidepressants; tetracyclines; therapeutic radiopharmaceuticals; therapeutic vaccines; thiazide diuretics; thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

"Large organic molecule" refers to an organic molecule of molecular weight greater than 1000 g/mol.

"Linking group" refers to an organic moiety that is used as an intermediate molecular section to attach an organic or inorganic compound to an edge region of a graphene substrate. Nonlimiting examples of linking groups include: —NH(CH$_2$)$_2$NH—; —NH(CH$_2$)$_3$NH—; —NH(CH$_2$)$_4$NH—; —NH(CH$_2$)$_5$NH—; —NH(CH$_2$)$_6$NH—; —NH(CH$_2$)$_2$O—; —NH(CH$_2$)$_3$O—; —NH(CH$_2$)$_4$O—; —NH(CH$_2$)$_5$O—; —NH(CH$_2$)$_6$O—; —NH(CH$_2$)O(CH$_2$)NH—; —NHCH$_2$C(O)—; —NH(CH$_2$)$_2$C(O)—; —NH(CH$_2$)$_3$C(O)—; —NH(CH$_2$)$_4$C(O)—; —NH(CH$_2$)$_5$C(O)—; —NH(CH$_2$)$_6$C(O)—; —NH(CH$_2$)$_2$O(CH$_2$)$_2$OC(O)—; —O(CH$_2$)$_2$NH—; —O(CH$_2$)$_3$NH—; —O(CH$_2$)$_4$NH—; —O(CH$_2$)$_5$NH—; —O(CH$_2$)$_6$NH—; —O(CH$_2$)$_2$O—; —O(CH$_2$)$_3$O—; —O(CH$_2$)$_4$O—; —O(CH$_2$)$_5$O—; —O(CH$_2$)$_6$O—; —O(CH$_2$)O(CH$_2$)NH—; —OCH$_2$C(O)—; —O(CH$_2$)$_2$C(O)—; —O(CH$_2$)$_3$C(O)—; —O(CH$_2$)$_4$C(O)—; —O(CH$_2$)$_5$C(O)—; —O(CH$_2$)$_6$C(O)—; —O(CH$_2$)$_2$O(CH$_2$)$_2$OC(O)—;

NHC₆H₄NHC(S)NH(CH₂)₆—OP(O)₂—; —S(CH₂)₆OP(O)₂—; —NH(CH₂)₃NHC(O)(CH₂)₅NHC(O)(CH₂)S—; —NHNHC(O)—(CH₂)₄C(O)NHN═; —NH(CH₂)₃NH(CH₂)₃NH—; —NH(CH₂)₃NH(CH₂)₃NHCH₂—.

"Natural binding compound" refers to a ligand for a molecular binding site that is produced by the same organism that produces the molecule with the binding site. Typically, the ligand binds to the binding site with a $K_D < 1$ μM or even <100 nM.

"Non-covalently" bound refers to formation of a non-covalent bond, which does not involve the sharing of electrons between at least two atoms. The strength of a covalent bond typically ranges from approximately 1 kcal/mol to approximately 10 kcal/mol.

"Non-edge region" of a graphene substrate refers to the area between lines or borders where the graphene substrate ends and either another material or an open space begins.

"Non-natural binding compound" refers to a synthetically produced ligand for a molecular binding site that is not produced by the same organism that produces the molecule with the binding site. Typically, the ligand binds to the binding site with a $K_D < 1$ μM or even <100 nM.

"Nucleic acid letter code" refers to the one letter code typically used for nucleic acids: adenine (A); cytosine (C); guanine (G); thymine (T); uracil (U).

"Oligonucleotide" refers to short single-stranded DNA or RNA molecules. Oligonucleotides typically include between about 2 and about 50 nucleotides, often between about 2 and about 35 nucleotides, and in certain cases between about 2 and about 20 nucleotides.

Where the oligonucleotide is a single stranded DNA molecule, a nonlimiting, generalized structure is as shown below:

$N_1N_2N_3N_4N_5N_6N_7N_8N_9N_{10}N_{11}N_{12}N_{13}N_{14}N_{15}N_{16}N_{17}N_{18}N_{19}N_{20}$ where $N_1$ is A, T, C or G; $N_2$ is A, T, C or G; $N_3$ is A, T, C or G; $N_4$ is A, T, C or G; $N_5$ is A, T, C, G, or no base; $N_6$ is A, T, C, G, or no base; $N_7$ is A, T, C, G, or no base; $N_8$ is A, T, C, G, or no base; $N_9$ is A, T, C, G, or no base; $N_{10}$ is A, T, C, G, or no base; $N_{11}$ is A, T, C, G, or no base; $N_{12}$ is A, T, C, G, or no base; $N_{13}$ is A, T, C, G, or no base; $N_{14}$ is A, T, C, G, or no base; $N_{15}$ is A, T, C, G, or no base; $N_{16}$ is A, T, C, G, or no base; $N_{17}$ is A, T, C, G, or no base; $N_{18}$ is A, T, C, G, or no base; $N_{19}$ is A, T, C, G, or no base; $N_{20}$ is A, T, C, G, or no base.

Where the oligonucleotide is a single stranded RNA molecule, a nonlimiting, generalized structure is as shown below:

$R_1R_2R_3R_4R_5R_6R_7R_8R_9R_{10}R_{11}R_{12}R_{13}R_{14}R_{15}R_{16}R_{17}R_{18}R_{19}R_{20}$ where $R_1$ is A, U, C, or G; $R_2$ is A, U, G, or C; $R_3$ is A, U, G, or C; $R_4$ is A, U, G, or C; $R_5$ is A, U, G, or C; $R_6$ is A, U, G, C or no base; $R_7$ is A, U, G, C or no base; $R_8$ is A, U, G, C or no base; $R_9$ is A, U, G, C or no base; $R_{10}$ is A, U, G, C or no base; $R_{11}$ is A, U, G, C or no base; $R_{12}$ is A, U, G, C or no base; $R_{13}$ is A, U, G, C or no base; $R_{14}$ is A, U, G, C or no base; $R_{15}$ is A, U, G, C or no base; $R_{16}$ is A, U, G, C or no base; $R_{17}$ is A, U, G, C or no base; $R_{18}$ is A, U, G, C or no base; $R_{19}$ is A, U, G, C or no base; $R_{20}$ is A, U, G, C or no base.

"Oligopeptide" refers to a short chain of amino acids. Oligopeptides typically include between about 2 and about 25 amino acids. A nonlimiting, generalized structure for oligopeptides is shown below:

$P_1P_2P_3P_4P_5P_6P_7P_8P_9P_{10}P_{11}P_{12}P_{13}P_{14}P_{15}P_{16}P_{17}P_{18}P_{19}P_{20}P_{21}P_{22}P_{23}P_{24}P_{25}$ where $P_1$ is G, P, A, V, L, I M, C, R, Y, W, H, K, R, Q, N, E, D, S or T; $P_2$ is G, P, A, V, L, I M, C, R, Y, W, H, K, R, Q, N, E, D, S or T; $P_3$ is G, P, A, V, L, I M, C, R, Y, W, H, K, R, Q, N, E, D, S or T; $P_4$ is G, P, A, V, L, I M, C, R, Y, W, H, K, R, Q, N, E, D, S or T; $P_5$ is G, P, A, V, L, I M, C, R, Y, W, H, K, R, Q, N, E, D, S or T; $P_6$ is G, P, A, V, L, I M, C, R, Y, W, H, K, R, Q, N, E, D, S, T or no amino acid; $P_7$ is G, P, A, V, L, I M, C, R, Y, W, H, K, R, Q, N, E, D, S, T or no amino acid; $P_8$ is G, P, A, V, L, I M, C, R, Y, W, H, K, R, Q, N, E, D, S, T or no amino acid; $P_9$ is G, P, A, V, L, I M, C, R, Y, W, H, K, R, Q, N, E, D, S, T or no amino acid; $P_{10}$ is G, P, A, V, L, I M, C, R, Y, W, H, K, R, Q, N, E, D, S, T or no amino acid; $P_{11}$ is G, P, A, V, L, I M, C, R, Y, W, H, K, R, Q, N, E, D, S, T or no amino acid; $P_{12}$ is G, P, A, V, L, I M, C, R, Y, W, H, K, R, Q, N, E, D, S, T or no amino acid; $P_{13}$ is G, P, A, V, L, I M, C, R, Y, W, H, K, R, Q, N, E, D, S, T or no amino acid; $P_{14}$ is G, P, A, V, L, I M, C, R, Y, W, H, K, R, Q, N, E, D, S, T or no amino acid; $P_{15}$ is G, P, A, V, L, I M, C, R, Y, W, K, R, Q, N, E, D, S, T or no amino acid; $P_{16}$ is G, P, A, V, L, I M, C, R, W, H, K, R, Q, N, E, D, S, T or no amino acid; $P_{17}$ is G, P, A, V, L, I M, C, R, Y, W, H, K, R, Q, N, E, D, S, T or no amino acid; $P_{18}$ is G, P, A, V, L, I M, C, R, Y, W, H, K, R, Q, N, E, D, S, T or no amino acid; $P_{19}$ is G, P, A, V, L, M, C, R, Y, W, H, K, R, Q, N, E, D, S, T or no amino acid; $P_{20}$ is G, P, A, V, L, M, C, R, Y, W, H, K, R, Q, N, E, D, S, T or no amino acid; $P_{21}$ is G, P, A, V, L, M, C, R, Y, W, H, K, R, Q, N, E, D, S, T or no amino acid; $P_{22}$ is G, P, A, V, L, I M, C, R, Y, W, H, K, R, Q, N, E, D, S, T or no amino acid; $P_{23}$ is G, P, A, V, L, I M, C, R, Y, W, H, K, R, Q, N, E, D, S, T or no amino acid; $P_{24}$ is G, P, A, V, L, M, C, R, Y, W, H, K, R, Q, N, E, D, S, T or no amino acid; $P_{25}$ is G, P, A, V, L, I M, C, R, Y, W, H, K, R, Q, N, E, D, S, T or no amino acid.

"Oligosaccharide" refers to refers to a short chain of monosaccharides. Oligosaccharides typically include between about 2 and about 25 monosaccharides. A nonlimiting, generalized structure for oligosaccharides is shown below:

$S_1S_2S_3S_4S_5S_6S_7S_8S_9S_{10}S_{11}S_{12}S_{13}S_{14}S_{15}S_{16}S_{17}S_{18}S_{19}S_{20}S_{21}S_{22}S_{23}S_{24}S_{25}$ where $S_1$ is glucose, fructose, glucopyranose, ribitol, gluconic acid, glucosamine, or N-acetylneuraminide; $S_2$ is glucose, fructose, glucopyranose, ribitol, gluconic acid, glucosamine, or N-acetylneuraminide; $S_3$ is glucose, fructose, glucopyranose, ribitol, gluconic acid, glucosamine, N-acetylneuraminide or no monosaccharide; $S_4$ is glucose, fructose, glucopyranose, ribitol, gluconic acid, glucosamine, N-acetylneuraminide or no monosaccharide; $S_5$ is glucose, fructose, glucopyranose, ribitol, gluconic acid, glucosamine, N-acetylneuraminide or no monosaccharide; $S_6$ is glucose, fructose, glucopyranose, ribitol, gluconic acid, glucosamine, N-acetylneuraminide or no monosaccharide; $S_7$ is glucose, fructose, glucopyranose, ribitol, gluconic acid, glucosamine, N-acetylneuraminide or no monosaccharide; $S_8$ is glucose, fructose, glucopyranose, ribitol, gluconic acid, glucosamine, N-acetylneuraminide or no monosaccharide; $S_9$ is glucose, fructose, glucopyranose, ribitol, gluconic acid, glucosamine, N-acetylneuraminide or no monosaccharide; $S_{10}$ is glucose, fructose, glucopyranose, ribitol, gluconic acid, glucosamine, N-acetylneuraminide or no monosaccharide; $S_{11}$ is glucose, fructose, glucopyranose, ribitol, gluconic acid, glucosamine, N-acetylneuraminide or no monosaccharide; $S_{12}$ is glucose, fructose, glucopyranose, ribitol, gluconic acid, glucosamine, N-acetylneuraminide or no monosaccharide; $S_{13}$ is glucose, fructose, glucopyranose, ribitol, gluconic acid, glucosamine, N-acetylneuraminide or no monosaccharide; $S_{14}$ is glucose, fructose, glucopyranose, ribitol, gluconic acid, glucosamine, N-acetylneuraminide or no monosaccharide; $S_{15}$ is glucose, fructose, glucopyranose, ribitol, gluconic acid, glucosamine, N-acetylneuraminide or no monosaccharide; $S_{16}$ is glucose, fructose, glucopyranose, ribitol, gluconic acid, glucosamine, N-acetylneuraminide or no monosaccharide; $S_{17}$ is glucose, fructose, glucopyranose, ribitol, gluconic acid, glucosamine, N-acetylneuraminide or no monosaccharide; $S_{18}$ is glucose, fructose, glucopyranose, ribitol, gluconic acid, glucosamine, N-acetylneuraminide or no monosaccharide; $S_{19}$ is glucose, fructose, glucopyranose, ribitol, gluconic acid, glucosamine, N-acetylneuraminide or no monosaccharide; $S_{20}$ is glucose, fructose, glucopyranose, ribitol, gluconic acid, glucosamine, N-acetylneuraminide or no monosaccharide; $S_{21}$ is glucose, fructose, glucopyranose, ribitol, gluconic acid, glucosamine, N-acetylneuraminide or no monosaccharide; $S_{22}$ is glucose, fructose, glucopyranose, ribitol, gluconic acid, glucosamine, N-acetylneuraminide or no monosaccharide; $S_{23}$ is glucose, fructose, glucopyranose, ribitol, gluconic acid, glucosamine, N-acetylneuraminide or no monosaccharide; $S_{24}$ is glucose, fructose, glucopyranose, ribitol, gluconic acid, glucosamine, N-acetylneuraminide or no monosaccharide; $S_{25}$ is glucose, fructose, glucopyranose, ribitol, gluconic acid, glucosamine, N-acetylneuraminide or no monosaccharide.

"Organic molecule" refers to a molecule that includes carbon. Nonlimiting examples of organic molecules include: antibodies, antibody fragments, aptamers, oligonucleotides, oligopeptides, oligosaccharides, polynucleotides, polypeptides, polysaccharides, proteins, small molecule therapeutics, and large molecule therapeutics.

"Polynucleotide" refers to a single-stranded DNA or RNA molecule containing two or more nucleotides.

"Polypeptide" refers to a chain of two or more amino acids.

"Polysaccharide" refers to a chain or two or more monosaccharides.

"Protein" refers to a molecule made up of amino acids, typically long chains. A protein is usually necessary for a biological function and encoded by a gene within an organism. Classes of proteins include: structural proteins, storage proteins, defensive proteins, transport proteins, signal proteins, contractile proteins, and enzymes. Nonlimiting examples of proteins include: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab.

"Small molecule therapeutic" refers to an organic molecule of molecular weight less than 1000 g/mol, where the molecule has been, or is currently, used for a clinical application. Nonlimiting examples of small molecule therapeutic classes include: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; alternative medicines; amebicides; aminoglycosides; aminopenicillins; aminosalicylates; AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinson ism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer;

heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting anti-obesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracyclic antidepressants; tetracyclines; therapeutic radiopharmaceuticals; therapeutic vaccines; thiazide diuretics; thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

"Small organic molecule" refers to an organic molecule of molecular weight less than 1000 g/mol.

"Supporting substrate" refers to a second, different substrate onto which the graphene substrate can be adhered. Nonlimiting examples of such substrates include: organic polymers, metals, crystalline inorganic materials, non-crystalline inorganic materials, and ceramics.

"Van der Waals interaction" refers to the sum of the attractive forces between two molecules other than those due to covalent bonds, ionic bonds or hydrogen bonds. The strength of a Van der Waals interaction typically ranges from approximately 1 kcal/mol to approximately 2 kcal/mol.

The present invention relates to the functionalization of graphene substrates such as the one shown in FIG. 1. The referenced substrate (100), includes holes (130), edge regions (110) at the substrate/hole boundary and non-edge regions (120) that are in between the edge regions 110 and the outer boundary of substrate 100. One embodiment of the graphene substrate is graphene nanomesh.

Figure 2:
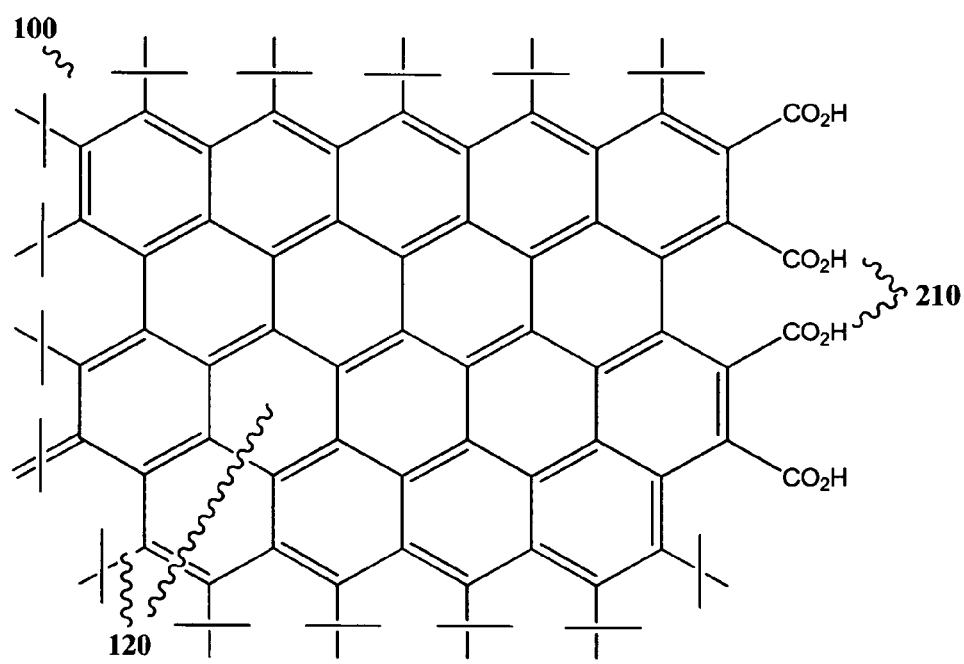
FIG. 2 is an illustration of a portion of a graphene substrate (100) having an edge functionalized with carboxylic acid groups (210) and non-edge regions (120).
Figure 3:
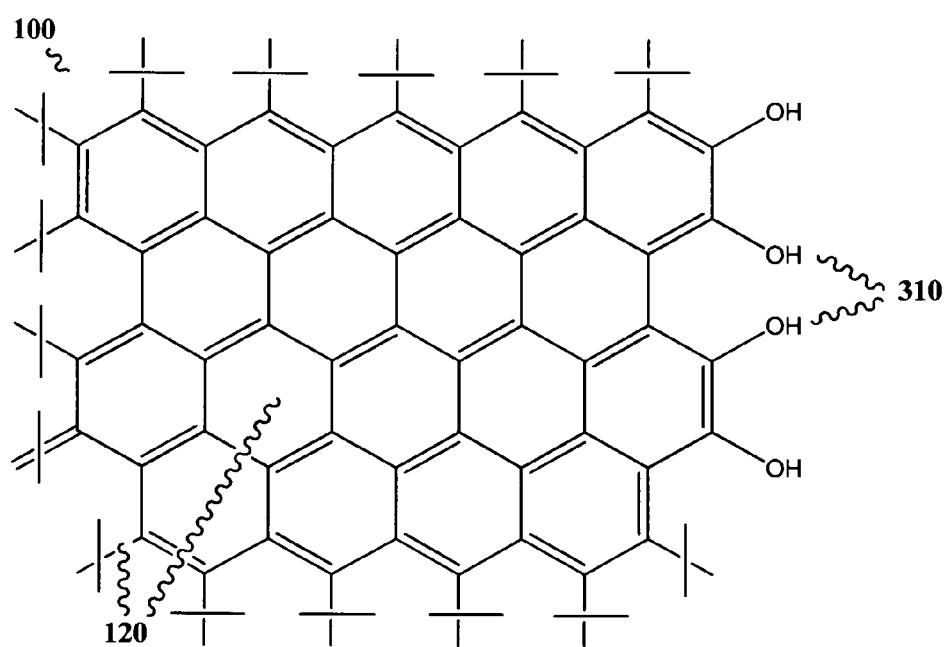
FIG. 3 is an illustration of a portion of a graphene substrate (100) having an edge functionalized with hydroxy groups (310) and non-edge regions (120).
Figure 4:
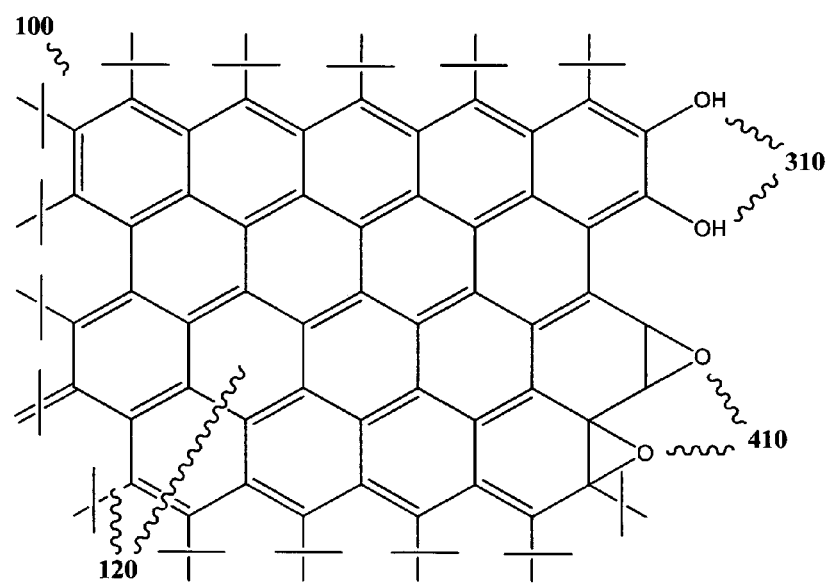
FIG. 4 is an illustration of a portion of a graphene substrate (100) having an edge functionalized with hydroxyl groups (310) and epoxy groups (410), and which contains non-edge regions (120).
Figure 5:
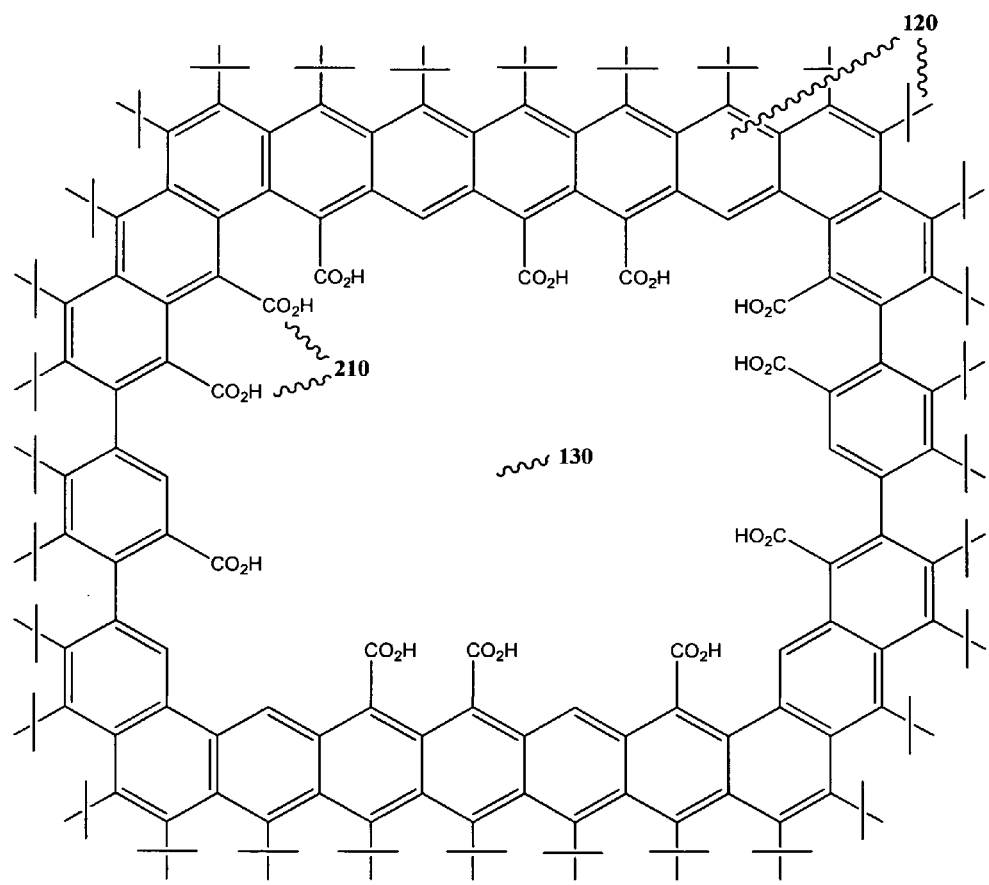
FIG. 5 is an illustration of a hole (130) within a graphene substrate having edges functionalized with carboxylic acid groups (210) and non-edge regions (120).

FIG. 2 shows a more detailed illustration of an edge region of a graphene substrate (100), where the edge includes oxidized carbon atoms in the form of carboxylic acid moieties (210), and a non-edge region (120). FIG. 3 shows a more detailed illustration of an edge region of a graphene substrate (100), where the edge includes oxidized carbon atoms in the form of hydroxy moieties (310), and a non-edge region (120). FIG. 4 shows a more detailed illustration of an edge region of a graphene substrate, where the edge includes oxidized carbon atoms in the form of hydroxy moieties (310) and epoxy moieties (410), and a non-edge region (120). FIG. 5 shows a more detailed illustration of a hole (130)/substrate interface where the edge includes oxidized carbon atoms in the form of carboxylic acid groups (210) and where the substrate has non-edge regions (120).

Figure 6:
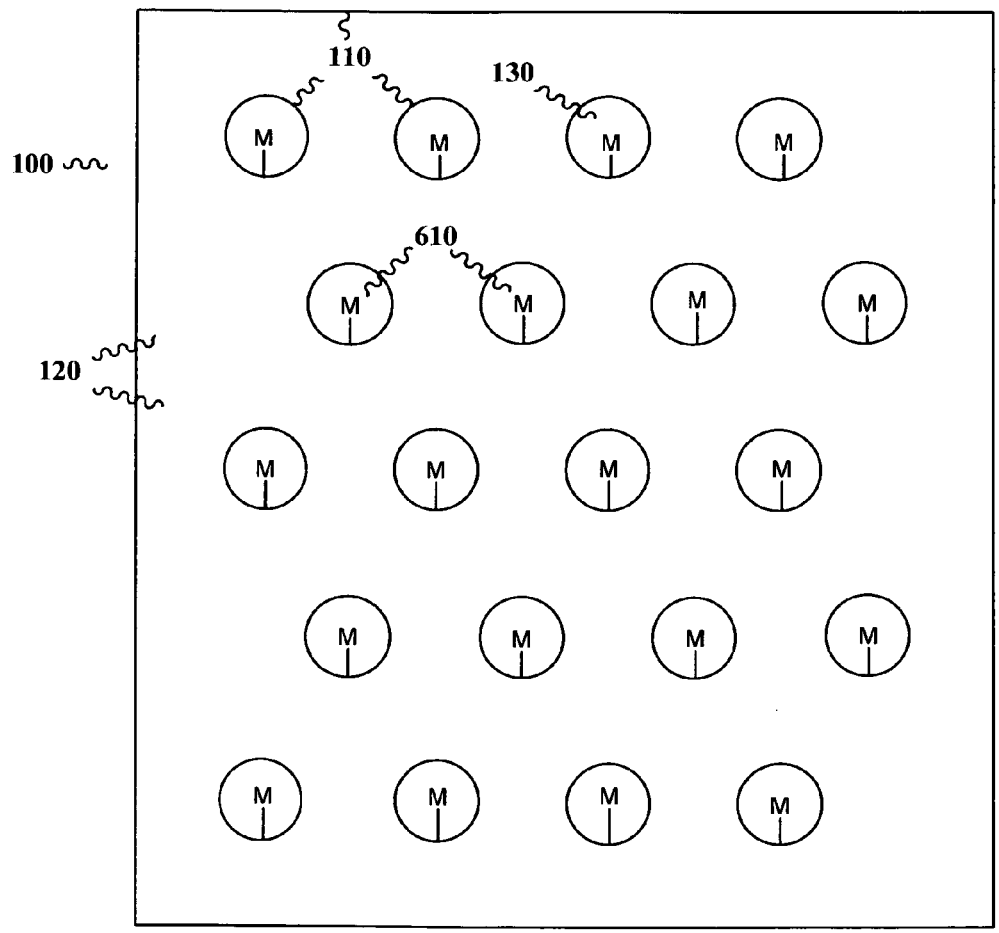
FIG. 6 is an illustration of a graphene substrate (100) having edge (110) and non-edge (120) regions, as well as holes (130) where there is no graphene, and where the edge regions are functionalized with one or more molecules (M, 610).

In a composition aspect, the present invention is directed to functionalized graphene substrates. FIG. 6 is an illustration of a graphene substrate (100) having edge (110) and non-edge (120) regions, as well as holes (130) where there is no graphene, and where the edge regions are functionalized with one or more molecules (M, 610). The functionalization occurs through addition to, or displacement of, oxidized moieties on the edge regions (110) (e.g., carboxylic acid moieties (210 of FIG. 2)).

Figure 7:
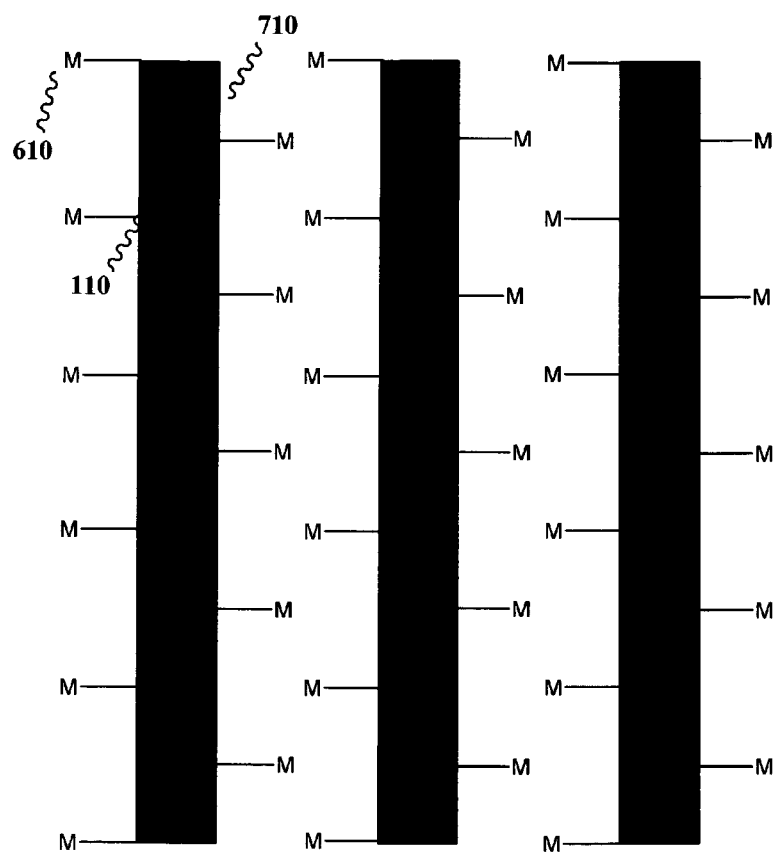
FIG. 7 is an illustration of three ribbons (710) of graphene substrates that have edge regions (110) that are functionalized with one or more molecules (M, 610).
Figure 8:
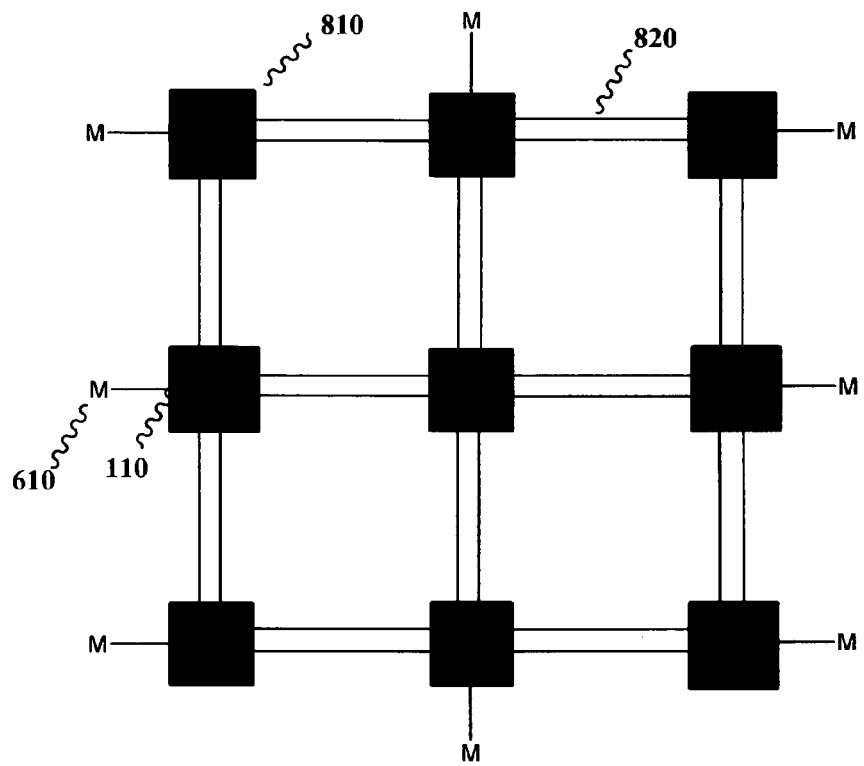
FIG. 8 is an illustration of graphene substrates (810) that have edge regions (110) that are functionalized with one or more molecules (M, 610), and which are connected with electrically conducting units (820).

Although a rectangular graphene substrate with perforations is shown in FIGS. 1 and 6, any suitable graphene substrate can be used. For instance, FIG. 7 is an illustration of three ribbons (710) of graphene substrates that have edge regions (110) that are functionalized with one or more molecules (M, 610). FIG. 8 is an illustration of graphene substrates (810) that have edge regions (110) that are functionalized with one or more molecules (M, 610), and which are connected with electrically conducting units (820).

Figure 9:
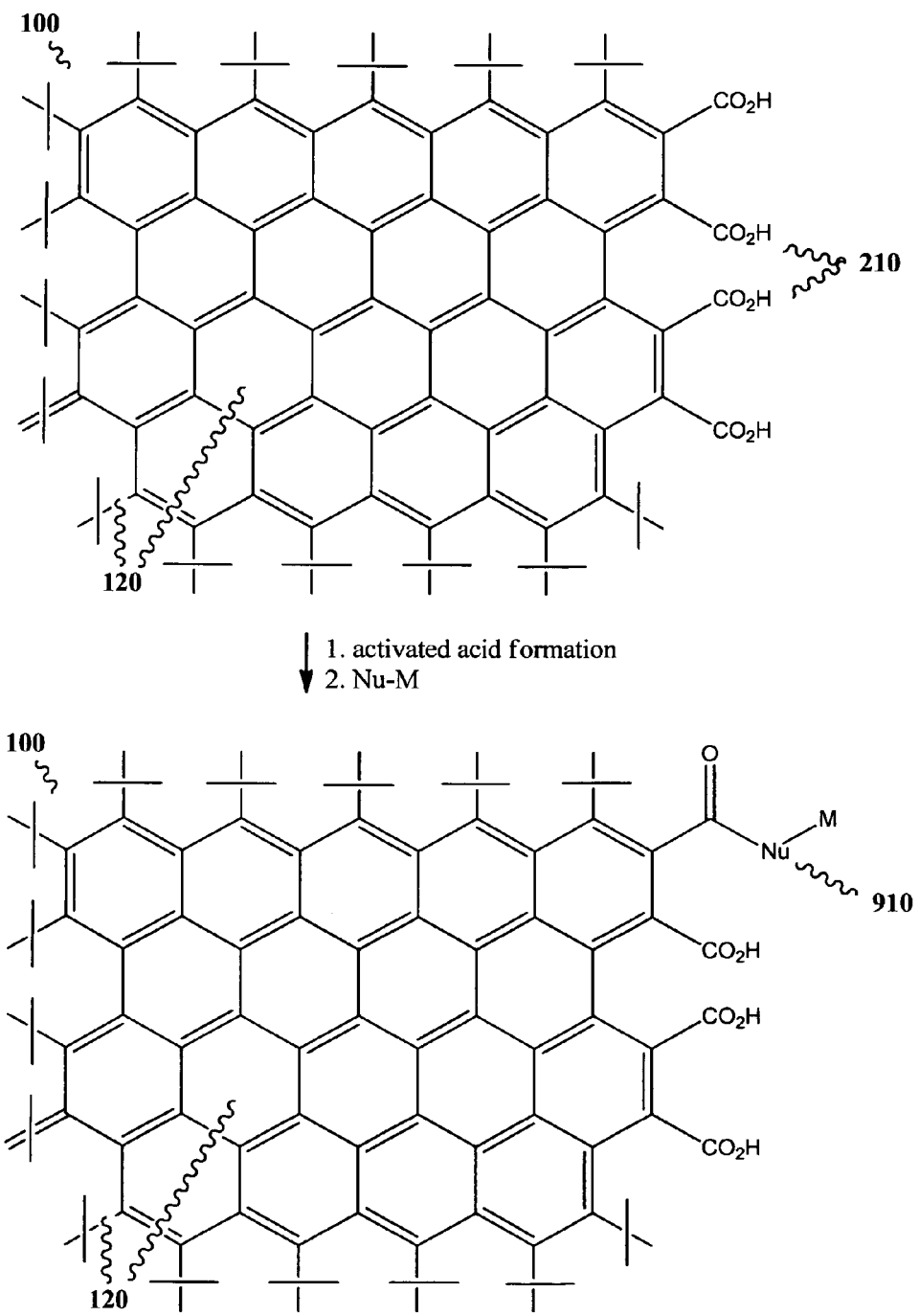
FIG. 9 is an illustration of the functionalization of carboxylic acid groups (210) through activation and subsequent reaction with a molecule NuM, where "Nu" is a nucleophilic moiety and "M" is an attached organic or inorganic moiety, to provide the functionalized group 910.

FIG. 9 is an illustration of the functionalization of carboxylic acid groups (210) through activation and subsequent reaction with a molecule NuM, where "Nu" is a nucleophilic moiety and "M" is an attached organic or inorganic moiety, to provide the functionalized group 910. Activation of 210 typically occurs through formation of a leaving group on, or in place of, the hydroxyl portion of the carboxylic acid. Nonlimiting examples of such activation include formation of the acid chloride (e.g., $SOCl_2$) or activated ester (e.g., DCC or EDC followed by N-hydroxysuccinimide condensation) corresponding to 210. "Nu" is any suitable nucleophilic moiety. Nonlimiting examples include $NH_2$-M (amide formation), HO-M (ester formation), HS-M (thioester formation). "M" is any suitable organic or inorganic moiety. Nonlimiting examples include $NH_2$-protein—where the $NH_2$ group ("Nu") is part of the native protein or the termination of a linking group attached to the protein—$NH_2$-oligopeptide—where the $NH_2$ group is part of the oligopeptide (e.g., termination of sidechain) or the termination of a linking group attached to the protein—$NH_2$-oligonucleotide—where the $NH_2$ group is the termination of a linking group attached to the oligonucleotide—$NH_2$-oligosaccharide—where the $NH_2$ group is the termination of a linking group attached to the oligonucleotide—$NH_2$-antibody—where the $NH_2$ group is part of the antibody or the termination of a linking group attached to the antibody—$NH_2$-[antibody fragment]—where the $NH_2$ group is part of the antibody fragment or the termination of a linking group attached to the antibody fragment—$NH_2$-aptamer—where the $NH_2$ group is the termination of a linking group attached to the aptamer—$NH_2$-[inorganic molecule]—where the $NH_2$ group is the termination of a linking group attached to the inorganic molecule—$NH_2$-[large molecule therapeutic]—where the $NH_2$ group is part of the large molecule therapeutic or the termination of a linking group attached to the large molecule therapeutic—$NH_2$-[organic molecule]—where the $NH_2$ group is part of the organic molecule or the termination of a linking group attached to the organic molecule—$NH_2$-[small molecule therapeutic]—where the $NH_2$ group is part of the small molecule therapeutic or the termination of a linking group attached to the small molecule therapeutic.

Figure 10:
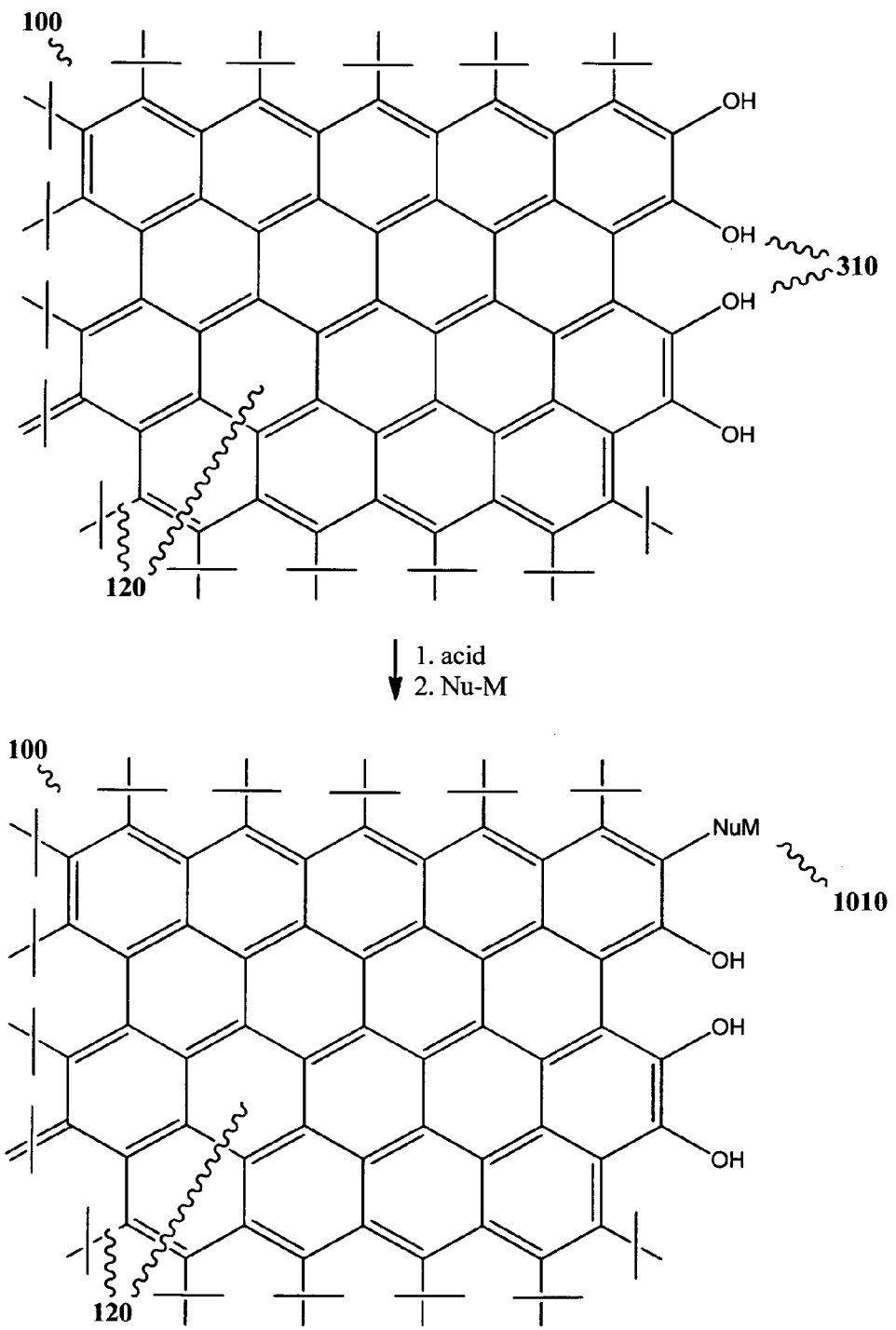
FIG. 10 is an illustration of the replacement of a hydroxyl group (310) on the edge of a graphene substrate (100) having non-edge regions (120) through acid catalysis and subsequent reaction with a molecule NuM, where "Nu" is a nucleophilic moiety and "M" is an attached organic or inorganic moiety, to provide functionalized group 1010.

FIG. 10 is an illustration of the replacement of a hydroxyl group (310) on the edge of a graphene substrate (100) having non-edge regions (120) through acid catalysis and subsequent reaction with a molecule NuM, where "Nu" is a nucleophilic moiety and "M" is an attached organic or inorganic moiety, to provide functionalized group 1010. "Nu" is any suitable nucleophilic moiety. Nonlimiting examples include $NH_2$-M (amide formation), HO-M (ester formation), HS-M (thioester formation). "M" is any suitable organic or inorganic moiety. Nonlimiting examples include $NH_2$-protein—where the $NH_2$ group ("Nu") is part of the native protein or the termination of a linking group attached to the protein—$NH_2$-oligopeptide—where the $NH_2$ group is part of the oligopeptide (e.g., termination of sidechain) or the termination of a linking group attached to the protein—$NH_2$-oligonucleotide—where the $NH_2$ group is the termination of a linking group attached to the oligonucleotide—$NH_2$-oligosaccharide—where the $NH_2$ group is the termination of a linking group attached to the oligonucleotide—$NH_2$-antibody—where the $NH_2$ group is part of the antibody or the termination of a linking group attached to the antibody—$NH_2$-[antibody fragment]—where the $NH_2$ group is part of the antibody fragment or the termination of a linking group attached to the antibody fragment—$NH_2$-aptamer—where the $NH_2$ group is the termination of a linking group attached to the aptamer—$NH_2$-[inorganic molecule]—where the $NH_2$ group is the termination of a linking group attached to the inorganic molecule—$NH_2$-[large molecule therapeutic]—where the $NH_2$ group is part of the large molecule therapeutic or the termination of a linking group attached to the large molecule therapeutic—$NH_2$-[organic molecule]—where the $NH_2$ group is part of the organic molecule or the termination of a linking group attached to the organic molecule—$NH_2$-[small molecule therapeutic]—where the $NH_2$ group is part of the small molecule therapeutic or the termination of a linking group attached to the small molecule therapeutic.

Figure 11:
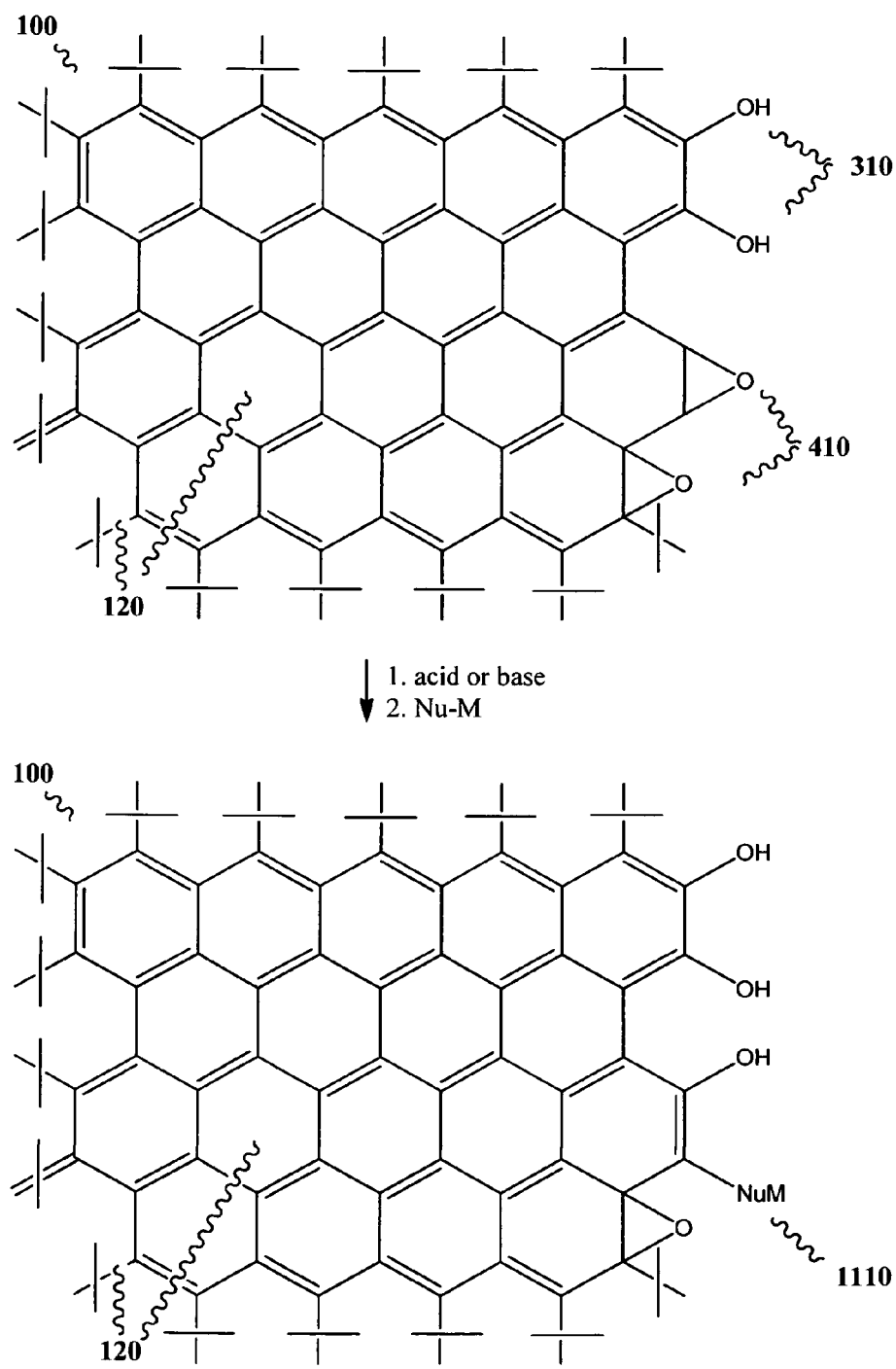
FIG. 11 is an illustration of the opening of an epoxy group (410) on the edge of a graphene substrate (100) having non-edge regions (120) through either acid or base catalysis and subsequent regarding with a molecule NuM, where "Nu" is a nucleophilic moiety and "M" is an attached organic or inorganic moiety, to provide functionalized group 1110.

FIG. 11 is an illustration of the opening of an epoxy group (410) on the edge of a graphene substrate (100) having non-edge regions (120) through either acid or base catalysis and subsequent regarding with a molecule NuM, where "Nu" is a nucleophilic moiety and "M" is an attached organic or inorganic moiety, to provide functionalized group 1110. "Nu" is any suitable nucleophilic moiety. Nonlimiting examples include $NH_2$-M (amide formation), HO-M (ester formation), HS-M (thioester formation). "M" is any suitable organic or inorganic moiety. Nonlimiting examples include $NH_2$-protein—where the $NH_2$ group ("Nu") is part of the native protein or the termination of a linking group attached to the protein—$NH_2$-oligopeptide—where the $NH_2$ group is part of the oligopeptide (e.g., termination of sidechain) or the termination of a linking group attached to the protein—$NH_2$-oligonucleotide—where the $NH_2$ group is the termination of a linking group attached to the oligonucleotide—$NH_2$-oligosaccharide—where the $NH_2$ group is the termination of a linking group attached to the oligonucleotide—$NH_2$-antibody— where the $NH_2$ group is part of the antibody or the termination of a linking group attached to the antibody—$NH_2$-[antibody fragment]—where the $NH_2$ group is part of the antibody fragment or the termination of a linking group attached to the antibody fragment—$NH_2$-aptamer—where the $NH_2$ group is the termination of a linking group attached to the aptamer—$NH_2$-[inorganic molecule]—where the $NH_2$ group is the termination of a linking group attached to the inorganic molecule—$NH_2$-[large molecule therapeutic]—where the $NH_2$ group is part of the large molecule therapeutic or the termination of a linking group attached to the large molecule therapeutic—$NH_2$-[organic molecule]—where the $NH_2$ group is part of the organic molecule or the termination of a linking group attached to the organic molecule—$NH_2$-[small molecule therapeutic]—where the $NH_2$ group is part of the small molecule therapeutic or the termination of a linking group attached to the small molecule therapeutic.

Figure 12:
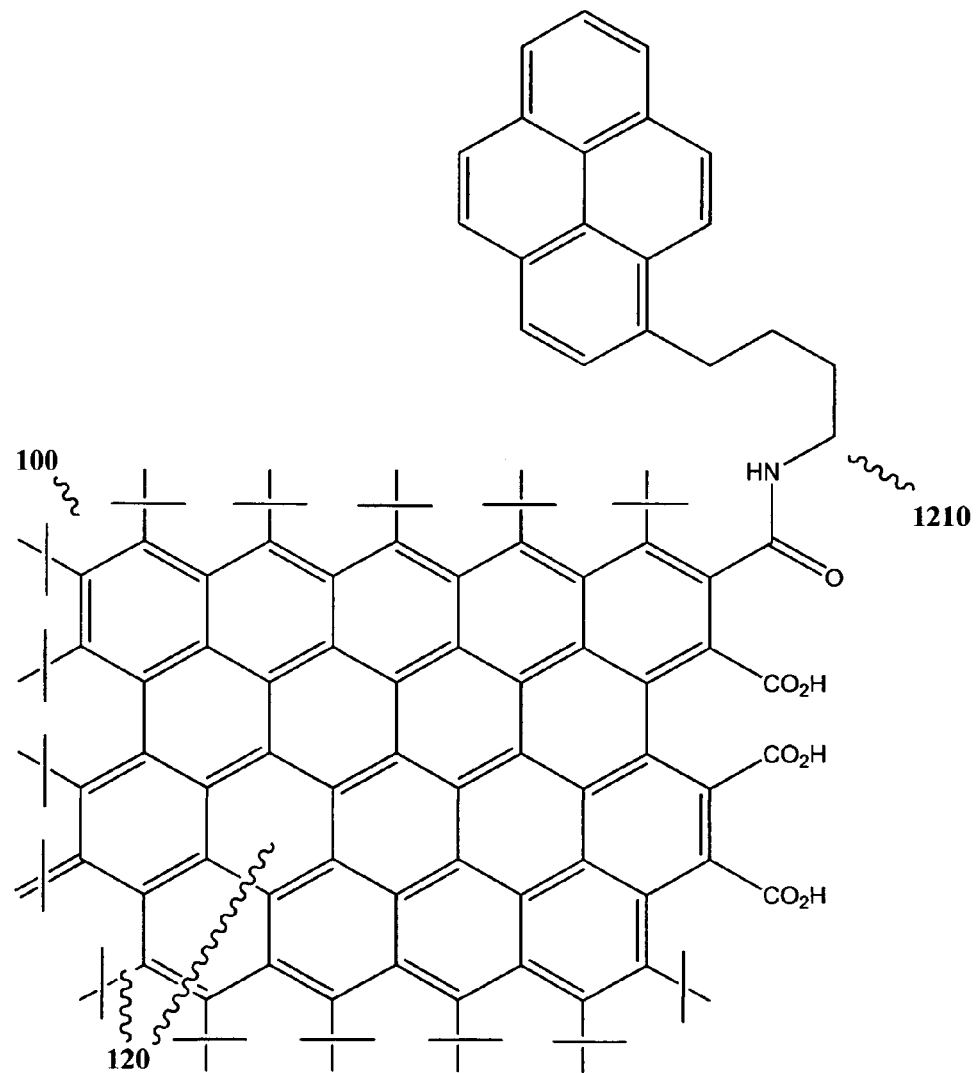
FIG. 12 is an illustration of a graphene substrate (100) functionalized on an edge with an amide containing a pyrene moiety (1210) and having non-edge regions (120).

FIG. 12 generally shows the functionalization of a carboxylic acid moiety with a Nu-M including a moiety that will promote pi-pi, noncovalent bonding with another aromatic pi system (e.g., pyrene containing molecule). Specifically, it shows an amide (1210) formed from a carboxylic acid moiety attached to a graphene substrate (100) including non-edge regions (120) where the NuM is $NH_2$—$(CH_2)_4$—$C_{15}H_9$.

Figure 13:
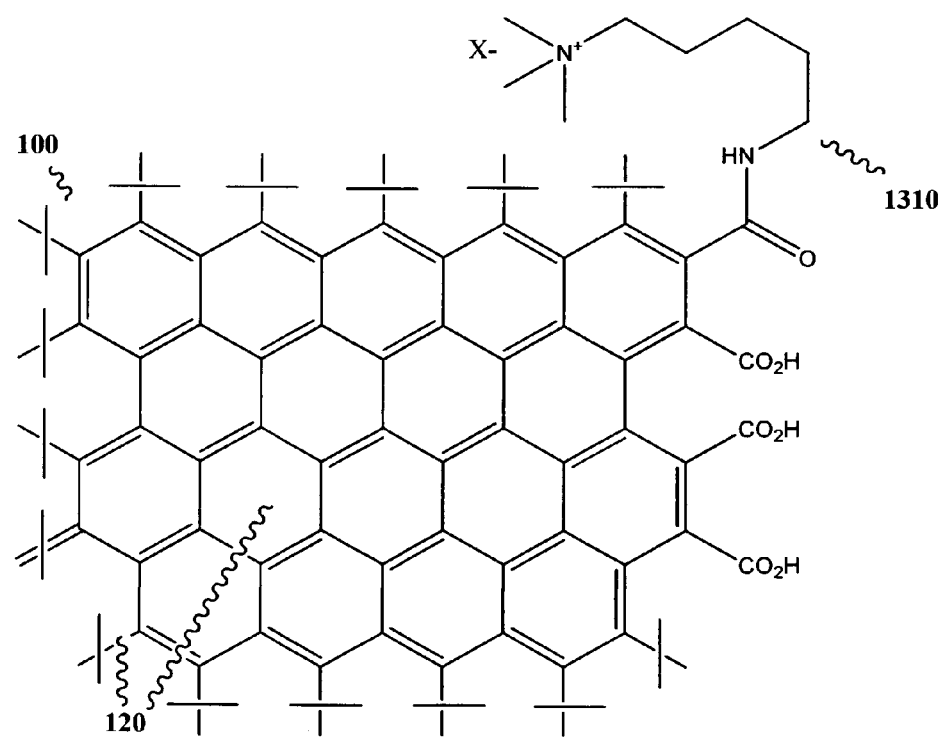
FIG. 13 is an illustration of a graphene substrate (100) functionalized on an edge with an amide containing an ammonium moiety (1310) and having non-edge regions (120).

FIG. 13 generally shows the functionalization of a carboxylic acid moiety with a Nu-M including a moiety that will promote ionic bond formation with a negatively charged molecule. The present invention also contemplates inclusion of a moiety that will promote ionic bond formation with a positively charged molecule—e.g., incorporating a carboxylic acid moiety that is negatively charged under conditions used to form the ionic bond. Specifically, it shows an amide (1310) formed from a carboxylic acid moiety attached to a graphene substrate (100) including non-edge regions (120) where the NuM is $NH_2$—$(CH_2)_5$—$N(CH_3)_3X$.

Figure 14:
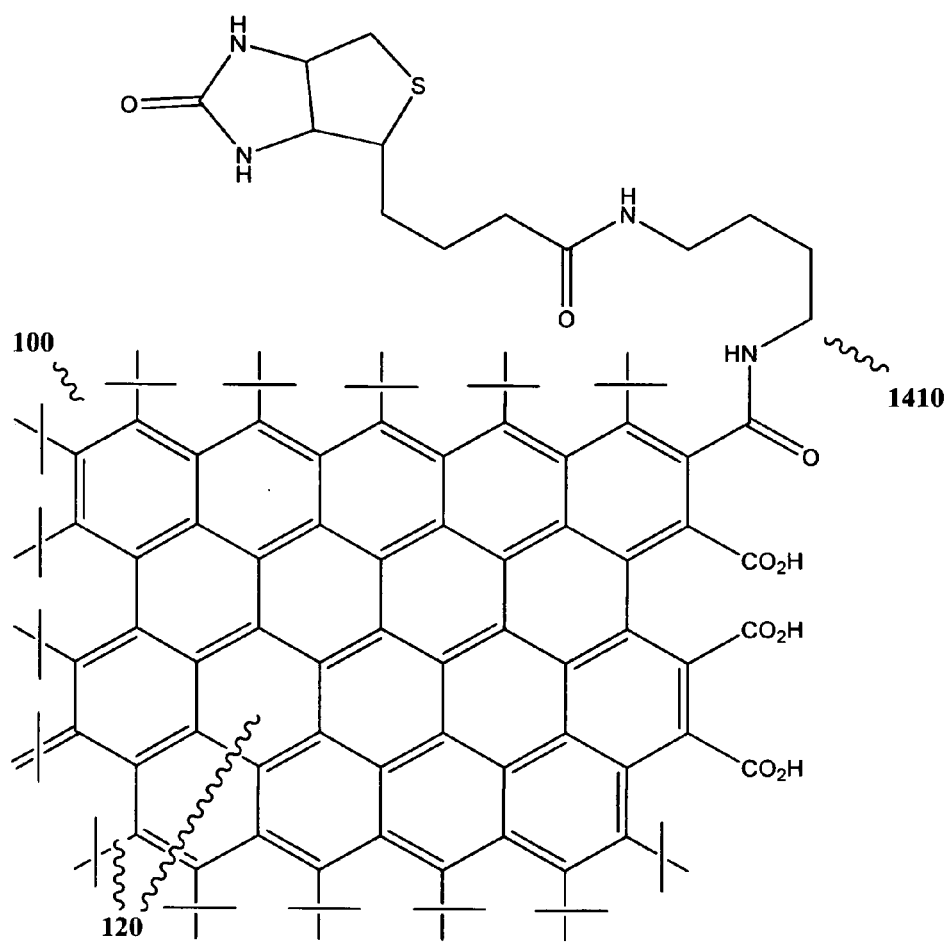
FIG. 14 is an illustration of a graphene substrate (100) functionalized on an edge with an amide containing a biotin moiety (1410) and having non-edge regions (120).

FIG. 14 generally shows the functionalization of a carboxylic acid moiety with a Nu-M including a moiety that will promote strong hydrogen bond formation. Specifically, it shows an amide (1410) formed from a carboxylic acid moiety attached to a graphene substrate (100) including non-edge regions (120) where the NuM is $NH_2$—$(CH_2)_4$—$NH(CO)$—$(CH_2)_3$—$C_5H_7N_2OS$ (biotin containing moiety).

Figure 15:
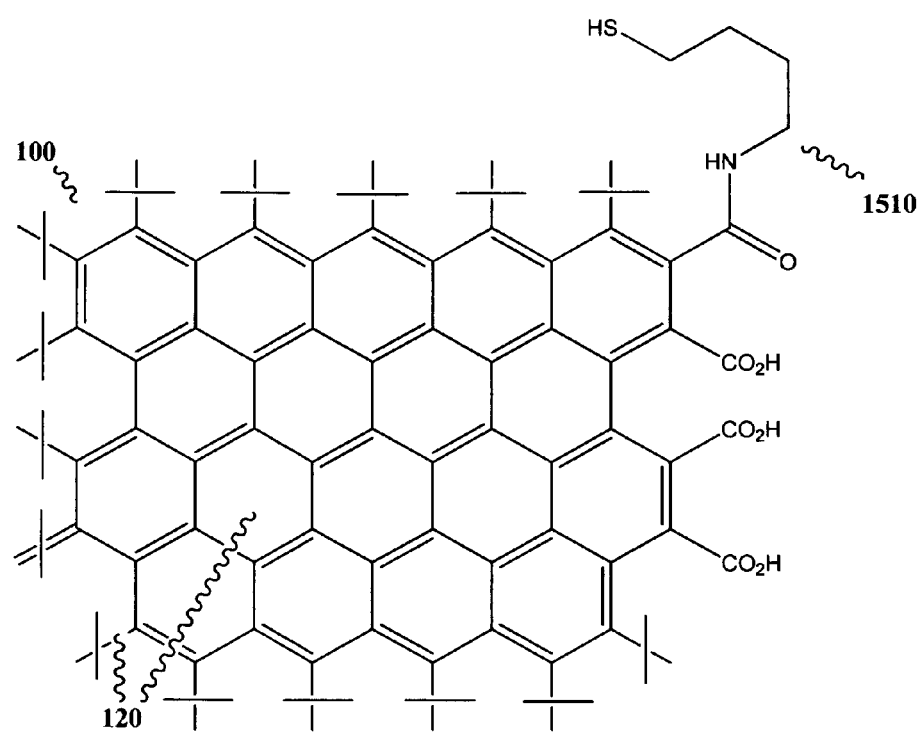
FIG. 15 is an illustration of a graphene substrate (100) functionalized on an edge with an amide containing a thiol moiety (1510) and having non-edge regions (120).

FIG. 15 generally shows the functionalization of a carboxylic acid moiety with a Nu-M including moiety that will promote disulfide bond formation. Specifically, it shows an amide (1510) formed from a carboxylic acid moiety attached to a graphene substrate (100) including non-edge regions (120) where the NuM is $NH_2$—$(CH_2)_4$—SH.

Any suitable functionalization chemistry may be used to functionalize a graphene substrate. The following are certain general conditions for functionalizing a graphene substrate with proteins and oligopeptides: The amine group (—$NH_2$) is the most common moiety used for attaching proteins to a graphene support. An amine group exists at the N-terminus of each polypeptide chain and in the side chain of certain amino acids (e.g., lysine). Nonlimiting examples of chemistries that can be used include: NHS ester-activation; aldehyde-activation; azlactone activation; and CDI activation.

Sulfhydryl groups on proteins (e.g., side chain of cysteine) may also be used to attach a protein to a graphene substrate. Nonlimiting examples of chemistries that can be used include: maleimide activation; iodoacetyl activation; and, pyridyl disulfide activation. Carboxyl groups on the proteins are also used to attach the molecules to a graphene substrate. EDC-mediated attachment is a typically used method.

General conditions for functionalizing a graphene substrate with oligonucleotides typically include amino, thiol or ACRYDITE™ modified oligonucleotides. An amino group can be attached to the 5' or 3' end of an oligonucleotide using standard chemistries. An amine modified oligonucleotide can be attached to a carboxyl group on the edge of a graphene substrate using carbodiimide, or other, reaction conditions. A thiol modifier can also be attached to the 5' or 3' end of an oligonucleotide. A thiol modified oligonucleotide can be attached to a graphene substrate, for example, by using maleimide, bromide, iodide or sulphonyl derivatives of the graphene edge region.

The following are general conditions for functionalizing a graphene substrate with oligosaccharides: formation of a hydrazide derivated using an activated carboxyl group on the edge region of the graphene substrate and subsequent reaction with an aldehyde moiety on the oligosaccharide.

The functionalized graphene substrates of the present invention include attached molecules (M) at certain populations per linear unit. If one considers the graphene edge as a linear section (e.g., circumference of a circle, perimeter of a rectangle, etc.), the molecules are present on the sections at a population of at least one molecule per 10,000 nm. In certain cases, the population is at least 10 molecules per 10,000 nm, at least 50 molecules per 10,000 nm, at least 100 molecules per 10,000 nm, at least 250 molecules per 10,000 nm, or at least 500 molecules per 10,000 nm.

Figure 16:
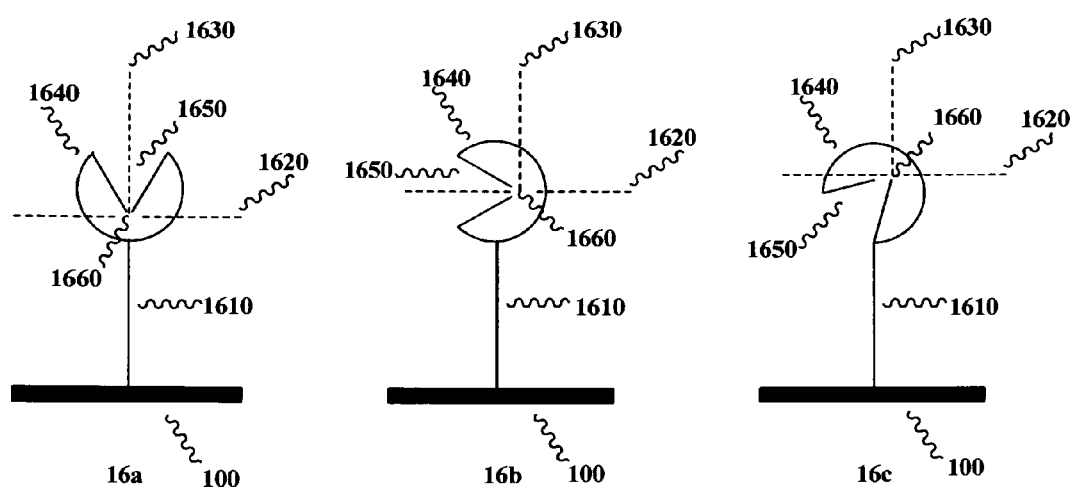
FIG. 16 is an illustration of a molecule (1640) bound to a graphene substrate (100) through a bond (1610), where a binding site (1650) on the molecule is defined by the intersection of dashed lines 1620 and 1630, which run through the center of the binding site (1660) in perpendicular directions.

FIG. 16 is an illustration of a molecule (1640) bound to a graphene substrate (100) through a bond (1610), where a binding site (1650) on the molecule is defined by the intersection of dashed lines 1620 and 1630, which run through the center of the binding site (1660) in perpendicular directions. The functionalized graphene substrate (100) of the present invention may include many different molecules having binding sites on its edge regions (110). With respect to molecules (1640), in the present invention more than twenty percent of them are bound in such a way that a conformation where the center of their binding site (1660) is bisected by line 1620 (as shown in FIG. 16b) is accessible at an energy level that is less than 20 kcal/mol above the conformational ground state. In certain cases, more than thirty percent, forty percent, or fifty percent are bound in that way. In certain cases the accessible energy level is less than 15 kcal/mol above the conformational ground state or 10 kcal/mol above the conformational ground state.

Figure 17:
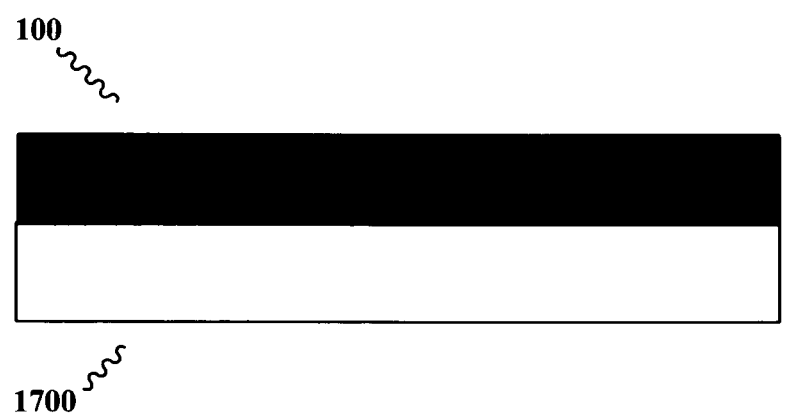
FIG. 17 is an illustration of a side view of a graphene substrate (100) adhered to a supporting substrate (1700).

In certain cases, the graphene substrate of the present invention is adhered to a supporting substrate. FIG. 17 is an illustration of a side view of a graphene substrate (100) adhered to a supporting substrate (1700). One method of forming a graphene substrate on a metallic or dielectric supporting substrate is discussed in US Pat. Appl. Pub. No. 20110091647, which was published on Apr. 21, 2011, and which is incorporated-by-reference for all purposes into this document. The graphene substrate synthesis method involves heating a metal or a dielectric on a substrate to a temperature between 400° C. and 1,400° C. The metal or dielectric is then exposed to an organic compound using chemical vapor deposition, thereby growing graphene on the metal or dielectric.

One method by which edge regions can be created internally, within a graphene substrate involves the creation of apertures or holes. The creation of such apertures or holes is discussed in US Pat. Appl. Pub. No. 20120048894, which was published on Mar. 1, 2012, and which is incorporated-by-reference for all purposes into this document. According to the publication, holes or apertures can be made by selective oxidation or be laser-drilled. Using the oxidation method discussed in *Nano Lett.* 2008, Vol. 8, No. 7, pgs 1965-1970, applicants were able to form apertures or holes in the 20 to 180 nm range in graphene substrates.

Furthermore, one may use, for example, a nanomeshed graphene substrate, which provides internal edge regions. The formation of such nanomeshes is discussed in US Pat. Appl. Pub. No. 20120301953, which was published on Nov. 29, 2012, and which is incorporated-by-reference for all purposes into this document.

The invention claimed is:

1. A graphene substrate, wherein the substrate comprises edge and non-edge regions, and wherein organic or inorganic molecules are bound to a nucleophilic moiety covalently linked to a carbon molecule in the edge regions of the substrate, and wherein the organic or inorganic molecules are present on the substrate edges at a population greater than about one molecule per 10,000 nm.

2. The graphene substrate according to claim 1, wherein organic molecules are present on the substrate, and wherein the organic molecules are selected from a group consisting of: antibodies; antibody fragments; aptamers; large molecule therapeutics; oligonucleotides; oligopeptides; oligopeptides, proteins and small molecule therapeutics.

3. The graphene substrate according to claim 2, wherein the population is greater than about 10 molecules per 10,000 nm.

4. The graphene substrate according to claim 3, wherein the organic molecules are selected from a group consisting of: antibodies; antibody fragments; proteins; and, aptamers.

5. The graphene substrate according to claim 3, wherein the organic molecules are selected from a group consisting of: large molecule therapeutics; oligonucleotides; oligopeptides; oligopeptides and small molecule therapeutics.

6. The graphene substrate according to claim 4, wherein the population is greater than about 50 molecules per 10,000 $nm^2$.

7. The graphene substrate according to claim 5, wherein the population is greater than about 50 molecules per 10,000 $nm^2$.

8. The graphene substrate according to claim 6, wherein the organic molecules are proteins, and wherein the proteins are selected from a group consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1; Interferon-γ1; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab.

9. A method of functionalizing a graphene substrate, wherein the method comprises the steps of:
   a) obtaining a graphene substrate that has edge regions and non-edge regions, wherein the edge regions comprise carboxylic acid moieties, epoxy moieties or hydroxyl moieties;
   b) reacting the carboxylic acid moieties, epoxy moieties or hydroxyl moieties with a Nu-M, wherein Nu is a nucleophilic moiety and M is an attached organic or inorganic moiety,
thereby functionalizing the graphene substrate.

10. The method according to claim 9, wherein edge regions comprise carboxylic acids.

11. The method according to claim 9, wherein Nu is $NH_2$, and wherein M is an attached organic moiety, and wherein the organic moiety is selected from a group of organic moieties consisting of: an antibody; a linking group attached to an antibody; an antibody fragment; a linking group attached to an antibody fragment; a linking group attached to an aptamer; a protein; a linking group attached to a protein; an oligopeptide; a linking group attached to an oligopeptide; a linking group attached to an oligosaccharide; a large molecule therapeutic; a linking group attached to a large molecule therapeutic; a small molecule therapeutic; a linking group attached to a small molecule therapeutic.

12. The method according to claim 11, wherein the organic molecule is a linking group attached to a protein, and wherein the protein is selected from a group consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab.

13. The method according to claim 12, wherein the functionalized graphene substrate has a population of organic molecules at the edge region of at least 1 per 10,000 nm.

14. The method according to claim 13, wherein the functionalized graphene substrate has a population of organic molecules at the edge region of at least 50 per 10,000 nm.

* * * * *